Figure 1:
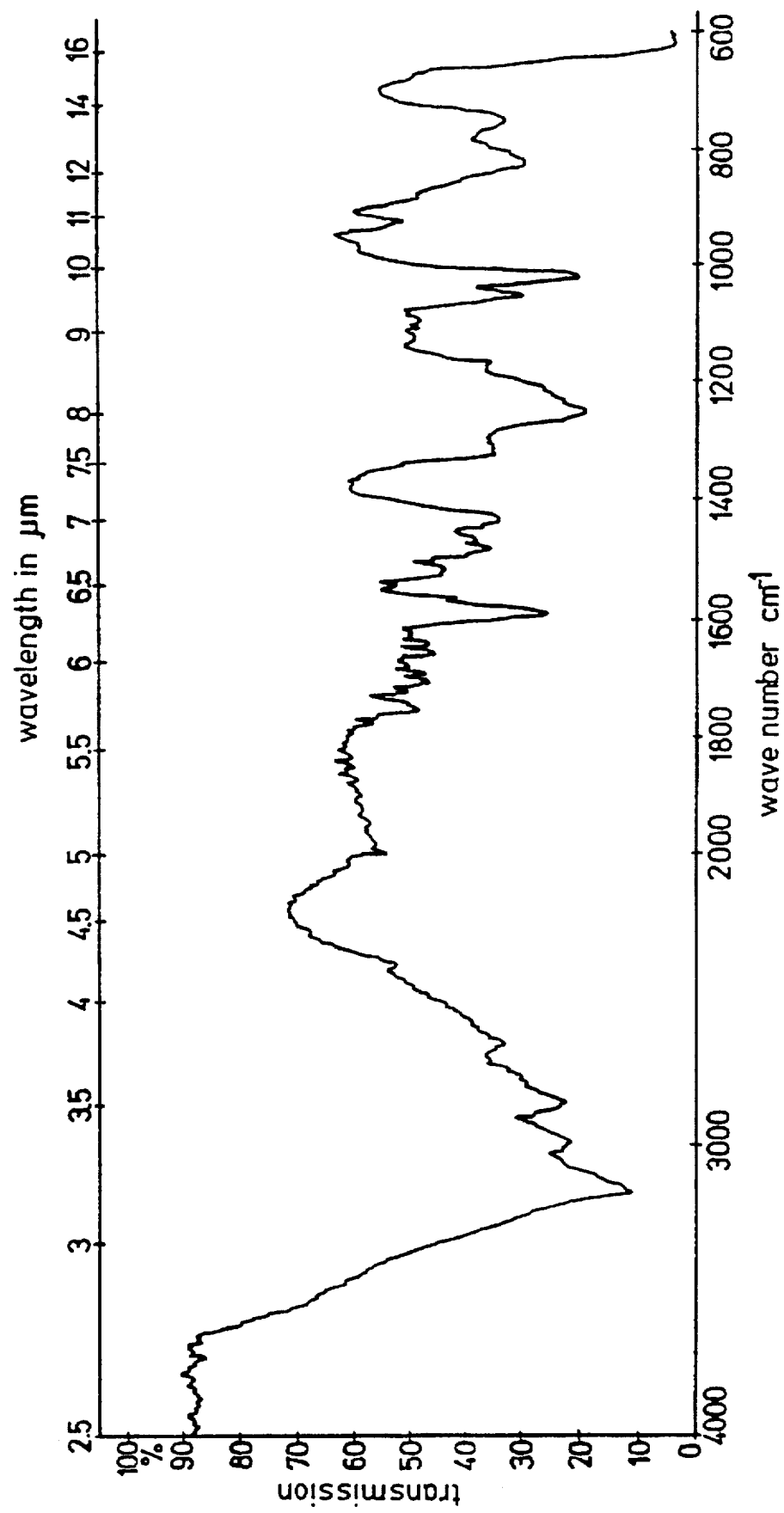

United States Patent [19]

Serra Mortes et al.

[11] Patent Number: 5,789,597

[45] Date of Patent: Aug. 4, 1998

[54] PROCESS FOR THE PREPARATION OF COMPOUNDS HAVING ACE INHIBITORY ACTION AND INTERMEDIATES IN SAID PROCESS

[75] Inventors: Sonia Serra Mortes; Alberto Palomo Coll. both of Barcelona, Spain; Rok Zupet, Ljubljana-Tacen, Slovenia

[73] Assignee: LEK, tovarna farmacevtskih in kemicnih izdelkov, d.d., Slovenia

[21] Appl. No.: 596,214

[22] PCT Filed: Jul. 13, 1995

[86] PCT No.: PCT/SI95/00017

§ 371 Date: Feb. 15, 1996

§ 102(e) Date: Feb. 15, 1996

[87] PCT Pub. No.: WO96/02564

PCT Pub. Date: Feb. 1, 1996

[30] Foreign Application Priority Data

Jul. 13, 1994 [SI] Slovenia .................. P-9400290
Dec. 21, 1994 [SI] Slovenia .................. P-9400450

[51] Int. Cl.$^6$ .............. C07D 211/30; C07D 233/26; C07D 487/02; C07D 495/00
[52] U.S. Cl. .............. 546/238; 548/334.5; 548/379.1; 548/409; 548/428; 548/452; 548/535; 564/428
[58] Field of Search .............. 546/238; 548/334.5, 548/379.1, 409, 428, 452, 535; 564/428

[56] References Cited

FOREIGN PATENT DOCUMENTS

| 0012401 | 6/1980 | European Pat. Off. . |
|---|---|---|
| 0468929 | 1/1992 | European Pat. Off. . |
| 2004804 | 1/1989 | Spain . |
| 2018906 | 5/1991 | Spain . |
| 2019545 | 6/1991 | Spain . |
| 9602564 | 2/1996 | WIPO . |

OTHER PUBLICATIONS

"Low Molecular Weight Proteins as Carriers for Renal Drug Targeting." Franssen et al., *J. Med. Chem.* 1992, 35, pp. 1246–1259.

*Primary Examiner*—Johann Richter
*Assistant Examiner*—Jane C. Osowecki
*Attorney, Agent, or Firm*—Law Offices Pollock, Vande Sande & Priddy

[57] ABSTRACT

There is disclosed a process for the preparation of compounds having ACE inhibitory action of the formula

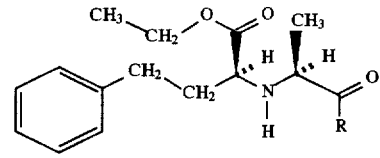

wherein R has the meanings as in claim 1, wherein the stereospecific amino acid N-|1-(S)-ethoxycarbonyl-3-phenylpropyl]-L-alanine is carboxylically activated with a thionyl chloride derivative wherein at least one chlorine atom is replaced by the residue of a heterocyclic ambident compound such as imidazole, benzimidazole, 2-methylimidazole or triazole, especially chlorothionylimidazole or thionyldiimidazole, in the presence of an organic solvent to the intermediate novel compound A or to the intermediate novel compound B and the obtained intermediate compound is reacted with an amino acid, preferably in the monosilylated form, most preferably in the disilylated form. Disclosed are also novel compounds useful as starting materials or intermediates in the present process.

21 Claims, 13 Drawing Sheets

PROCESS FOR THE PREPARATION OF COMPOUNDS HAVING ACE INHIBITORY ACTION AND INTERMEDIATES IN SAID PROCESS

This application is a 37-1 of PCT/SI95/00017 Jul. 13, 1995.

TECHNICAL FIELD

The present invention belongs to the field of the organic chemistry synthesis and refers to a process for the preparation of compounds having ACE inhibitory action as well as to novel compounds useful as starting materials or intermediates in the said process.

TECHNICAL PROBLEM

There was a need for a simple and industrially convenient process for the preparation of compounds having ACE inhibitory action.

PRIOR ART

In EP 0215335 there is disclosed a process for activating N-[1-(S)-ethoxycarbonyl-3-phenylpropyl]-L-alanine with phosgene or polymers thereof to N-[1-(S)-ethoxycarbonyl-3-phenylpropyl]-L-alanine N-carboxyanhydride. The reaction yields are very high but the process necessitates the use of a highly toxic reagent for the preparation of an active intermediate. During the reaction phosgene polymers decompose to phosgene, which leaves the reaction medium. A fresh reagent must be added repeatedly. For carrying out the process, special industrial plants are necessary in order to prevent the contamination of environment.

N-[1-(S)-ethoxycarbonyl-3-phenylpropyl]-L-alanine N-carboxyanhydride reacts with organic and inorganic salts of L-proline. Reactions take place in a basic medium as to prevent possible reactions with the secondary amino group.

It is well-known from the literature that for the formation of N-carboxyanhydrides of amino acids also carbonyl diimidazole may be used as a synthon for the formation of phosgene. The yields of acylation reaction depend upon the organic solvents used and water in the reaction solution. In methanol the reaction yield is 41.4%, in dioxane 96% and in acetone 94%. The reaction results are determined by HPLC analysis.

In the said patent in the activation reaction of the starting N-[1-(S)-ethoxycarbonyl-3-phenylpropyl]-L-alanine neither the racemization on α-C atom of N-[1-(S)-ethoxycarbonyl-3-phenylpropyl]-L-alanine N-carboxyanhydride is specified nor possible side reactions (J. Org. Chem., 32, 11, 1967) are mentioned. In the optimum Example 4 the reaction yield up to enalapril (base) is 87%. The separation of enalapril maleate is carried out with a 81.8% yield.

In U.S. Pat. No. 4,374,829 a process for the preparation of enalapril maleate by asymmetric reduction of the corresponding starting Schiff's base is disclosed. In different reaction conditions, however, always only a mixture of stereospecific isomers is isolated.

In ES patent 2,004,804 the preparation of carboxyalkyl-dipeptides useful as ACE inhibitors is disclosed. N-[1-(S)-ethoxycarbonyl-3-phenylpropyl]-L-alanine is treated with 1,1-carbonyldiimidazole in EtOAc and subsequently with L-proline and enalapril maleate is obtained with a 77% yield.

The Technical Solution

The first object of the invention is a process for the preparation of compounds having ACE inhibitory action of the formula

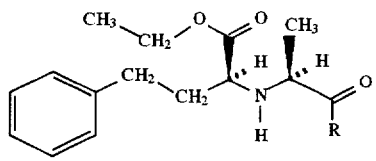

and pharmaceutically acceptable salts thereof, wherein R has the following meanings

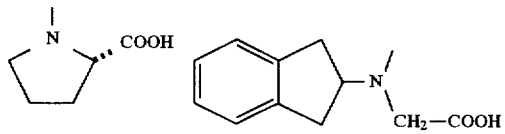

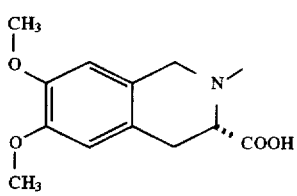

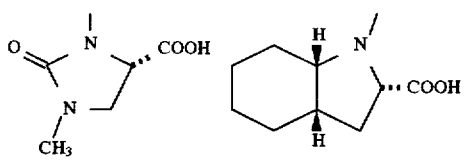

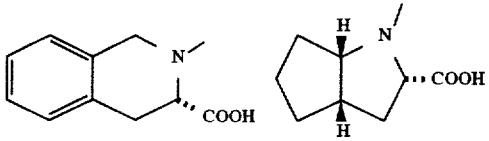

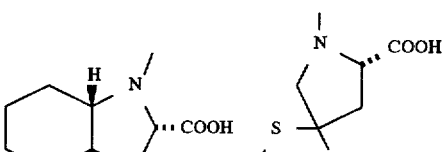

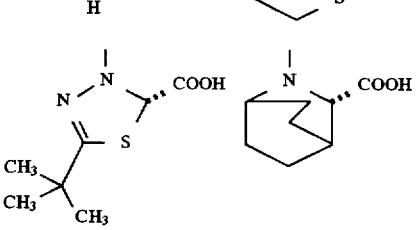

characterized in that the carboxy group of the stereospecific amino acid N-[1-(S)-ethoxycarbonyl-3-phenylpropyl]-L-alanine of the formula

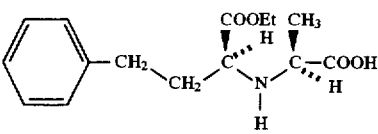

is activated with thionyl chloride derivative of the formula I'

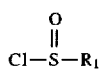

or with thionyl chloride derivative of the formula II'

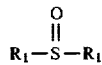

wherein $R_1$ is the residue of a heterocyclic ambident compound such as imidazole, benzimidazole, 2-methylimidazole or triazole, in the presence of an aprotic organic solvent under elimination of the precipitated hydrochloride of the above mentioned heterocyclic ambident compound, to the intermediate novel compound A

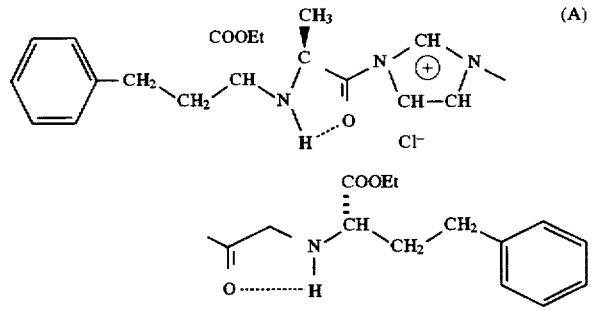

or to the intermediate novel compound B

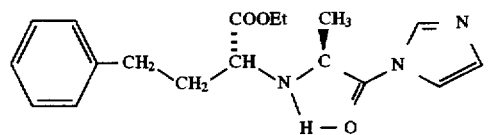

and the obtained intermediate compound (A, B) is reacted with an amino acid, preferably in its monosilylated form, most preferably in a disilylated form, selected from the group consisting of

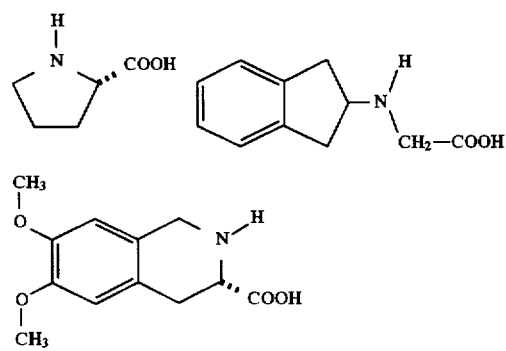

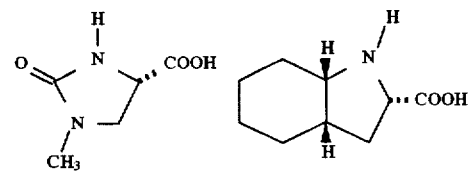

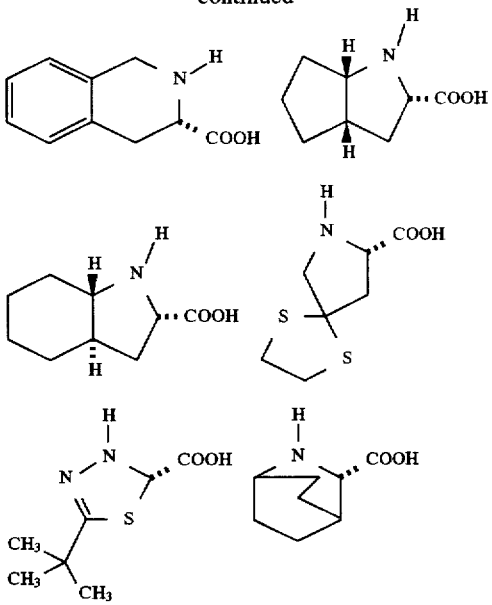

whereat the reaction medium must be anhydrous in all steps, and then the obtained compounds are converted to pharmaceutically acceptable salts thereof in a conventional manner.

The starting stereospecific amino acid N-[1-(S)-ethoxycarbonyl-3-phenylpropyl]-L-alanine is a well-known and commercially available compound and is disclosed in EP 353350 A1 and in Spanish Patent Application 9400994.

As the thionyl chloride derivative of the formula I' useful as the activating reagent e.g. chlorothionylimidazole of the formula (I)

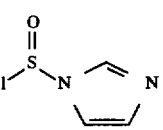

may be used and as the thionyl chloride derivative of the formula II' useful as the activating reagent e.g. thionyldiimidazole of the formula (II)

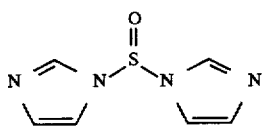

may be used.

The course of the activation of N-[1-(S)-ethoxycarbonyl-3-phenylpropyl]-L-alanine as the first process step of the inventive process using the reagent (I) is illustrated by Scheme 1.

SCHEME 1

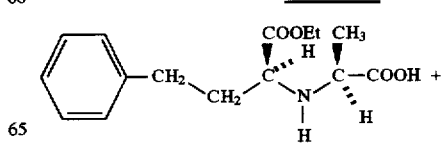

-continued
SCHEME 1

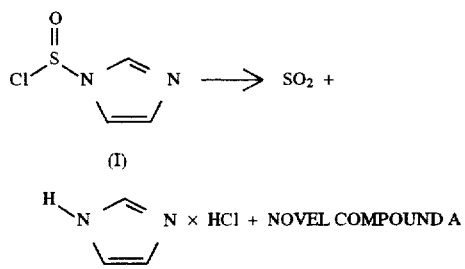

The obtained imidazole hydrochloride (ImHCl) must be eliminated several times since it coordinates either the starting stereospecific amino acid or the obtained novel intermediate A, B, thereby reducing the yield.

The organic solvents for the reaction are methylene chloride, dichloroethane, chloroform, toluene, benzene, heptane, hexane, whereas for the extraction and isolation of the final product the solvents are ethyl acetate, isopropyl acetate, t-butyl methyl ether. The reactions take place at temperatures from −20° C. to room temperature.

Chlorothionylimidazole of the formula (I) is a known compound. The IR spectrum thereof is shown in FIG. 1.

Thionyldiimidazole of the formula (II), m.p. 78°–79° C., was first synthesized by Staab in 1961 (Angew. Chem. 76, 26, 1961) and has never been used for the present purpose.

The remaining thionyl chloride derivatives useful as activating reagents are available compounds.

Activating reagents are convenient for the activation of amino acids and organic acids in general. Economically as well as ecologically, the said reagents are advantageous over phosgene and polymers thereof as well as over carbonyldiimidazole (CDI).

The compound of the formula (I) or the compound of the formula (II) are prepared by a reaction of thionyl cloride (SOCl$_2$) and imidazole in stoichiometric amounts and at temperatures in the range from −20° C. to +25° C.

The process for the preparation of the compound of the formula (I) is carried out in such a way that thionyl chloride is reacted with a stoichiometric molar amount of imidazole in an organic solvent under elimination of the formed imidazole hydrochloride (ImHCl).

Certain pharmaceutically acceptable salts of the compounds having ACE inhibitory action, of the above formula such as hydrochloride, sulfate and sodium salt are also novel and represent objects of invention.

As organic solvents the same solvents are used as in the process of activation of a stereospecific amino acid N-[1-(S)-ethoxycarbonyl-3-phenylpropyl]-L-alanine.

The preparation of the compounds of the formulas (I) or (II) is shown in the Scheme 2.

SCHEME 2

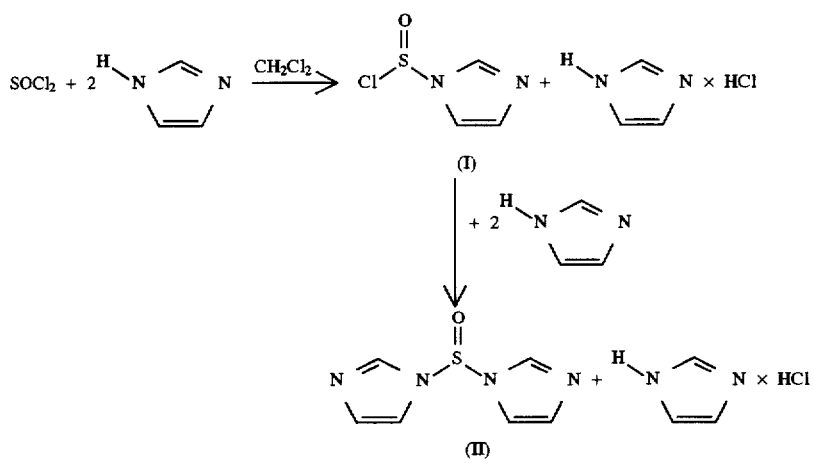

The test results show that the reaction yield of the obtained product depends upon the imidazole concentration in the reaction medium.

In the course of the reaction the filtration of imidazole hydrochloride is carried out twice. Im.HCl is sucked off for the first time in the preparation of reagents (I) and (II) and for the second time after the reaction of activation of the amino acid N-[1-(S)-ethoxycarbonyl-3-phenylpropyl]-L-alanine.

It is proceeded similarly in the preparation of the remaining activating reagents.

The process yield or the yield of the final product may be improved in such a way that the mixture of monosilylated and disilylated amino acids, preferably in the ratio 1:1, is used for the reaction with amino acid.

Namely, the effect of the reaction time on the formation of enalapril was observed. It was found that when starting from 1.4 g of N-[1-(S)-ethoxycarbonyl-3-phenylpropyl]-L-alanine and using L-proline as the amino acid, the yield of the isolated enalapril in the doubled reaction time was reduced from 1.85 g to 0.5 g. It was surprisingly found that this loss may be practically avoided if in the reaction of the intermediate compound a mixture with only a part of disilylated L-proline was used. The best results were obtained when a solution of silylated L-proline containing 50% of disilylated L-proline, i.e. L-proline-N-trimethylsilyl-O-trimethylsilyl ester of the formula

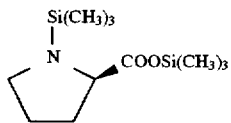

and 50% of monosilylated L-proline, i.e. L-proline-O-trimethylsilylester hydrochloride of the formula

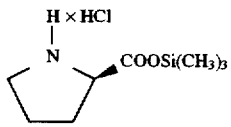

entered into the reaction and the reaction time was between 6 and 20 hours.

Thus a mixture of L-prolin-N-trimethylsilyl-O-trimethylsilyl ester and L-prolin-O-trimethylsilylester hydrochloride in a 1:1 ratio was used especially preferably as the amino acid.

Figure 3:
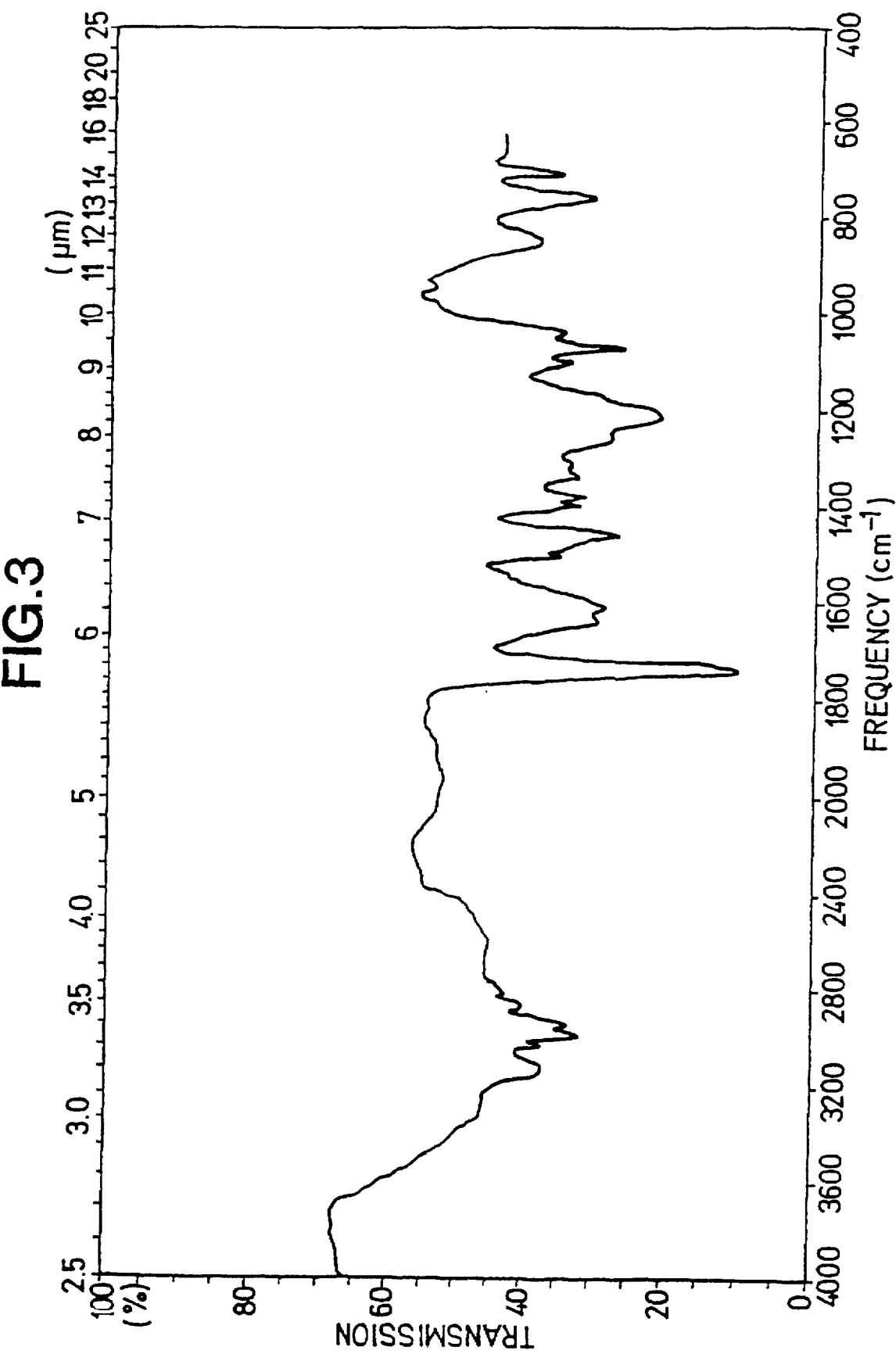
Figure 3A:
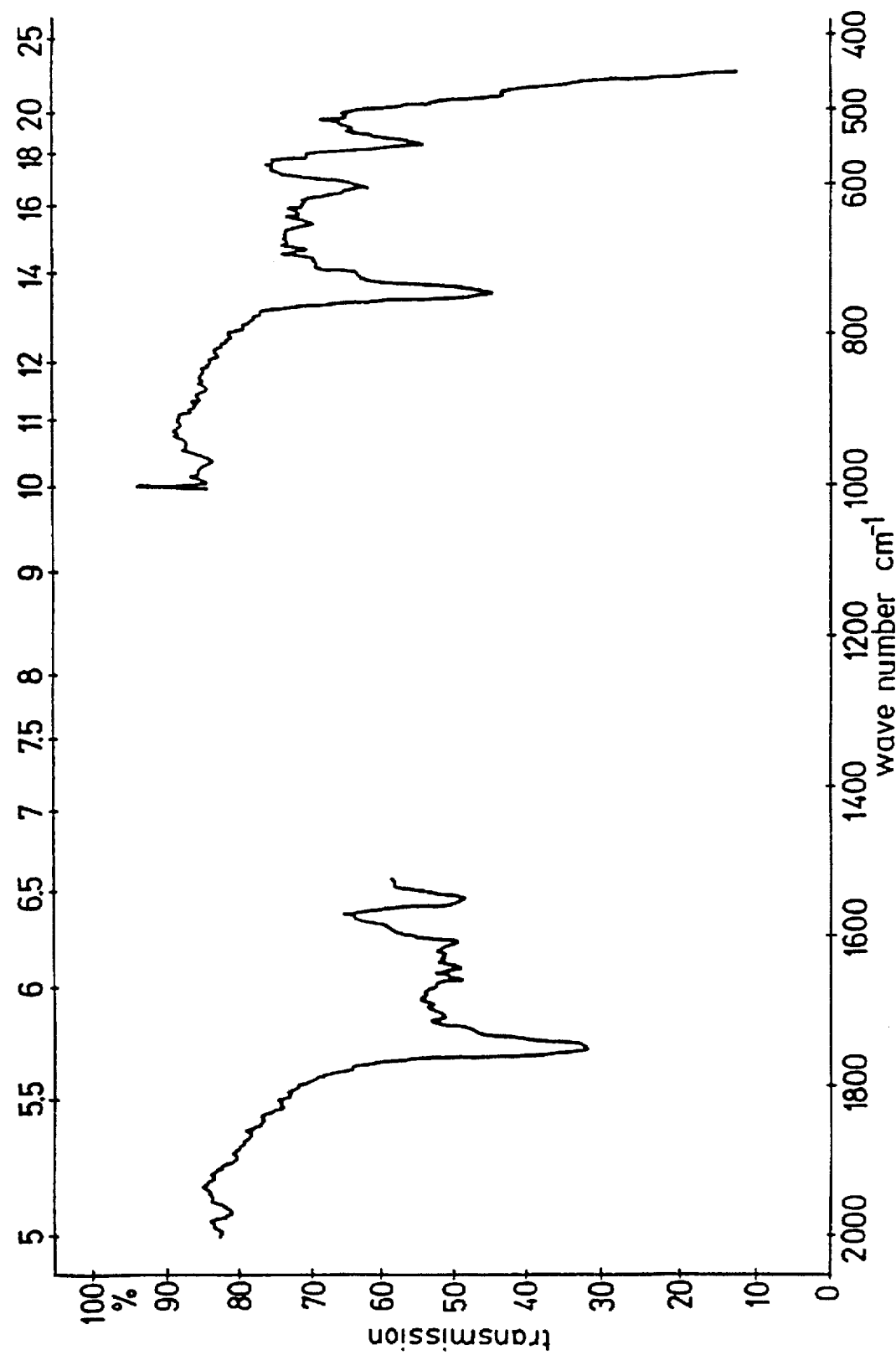
Figure 5:
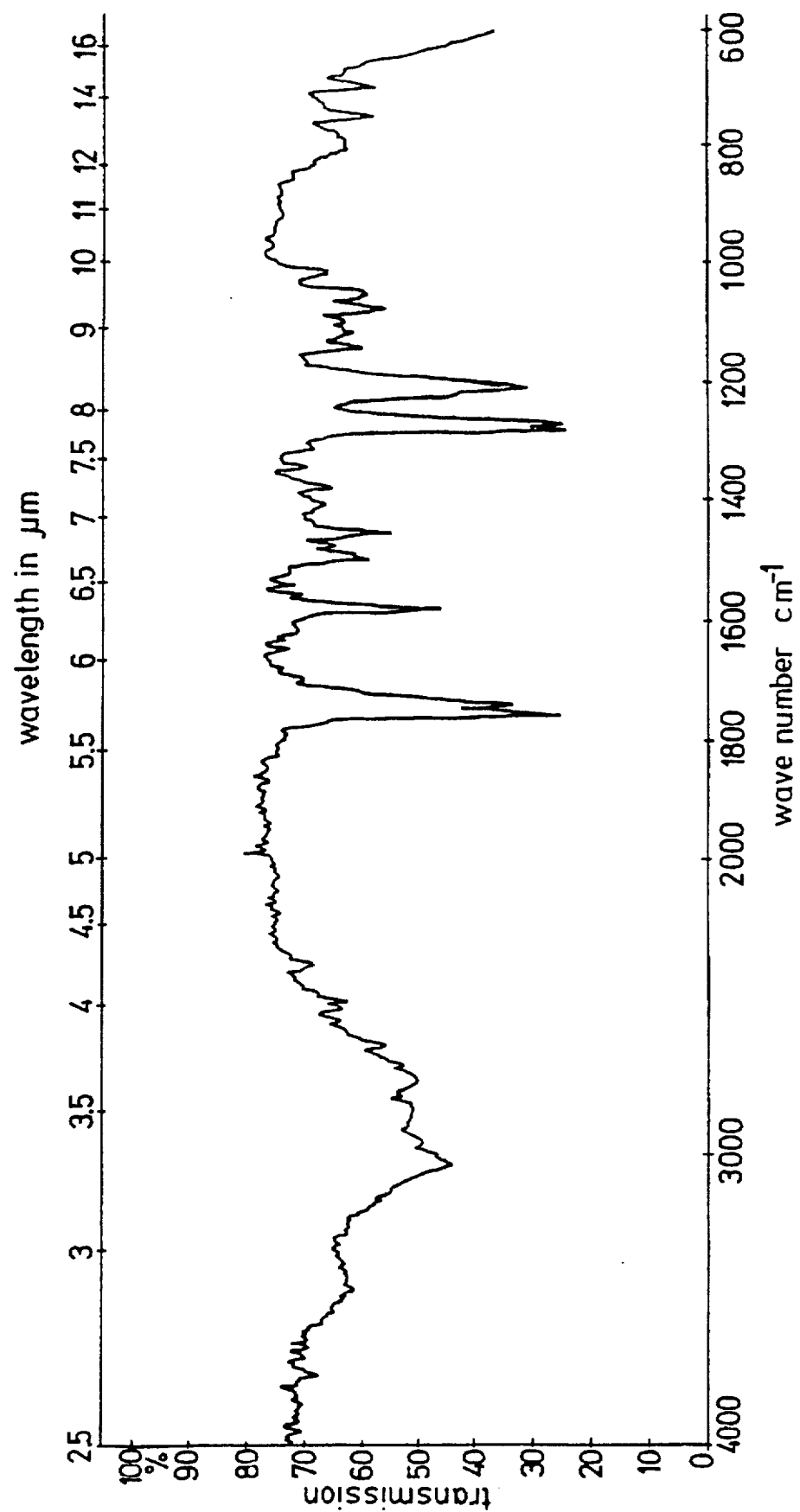

The intermediate compounds A and B are novel. The structure of the novel compound A, whose IR spectrum is shown in FIGS. 3 and 3a, is confirmed by the following findings:

1) On the basis of the IR spectrum (FIG. 3) and by comparison thereof with the IR spectrum of the N-[1-(S)-ethoxycarbonyl-3-phenylpropyl]-L-alanine acid chloride (FIG. 5) of the formula

Figure 2:
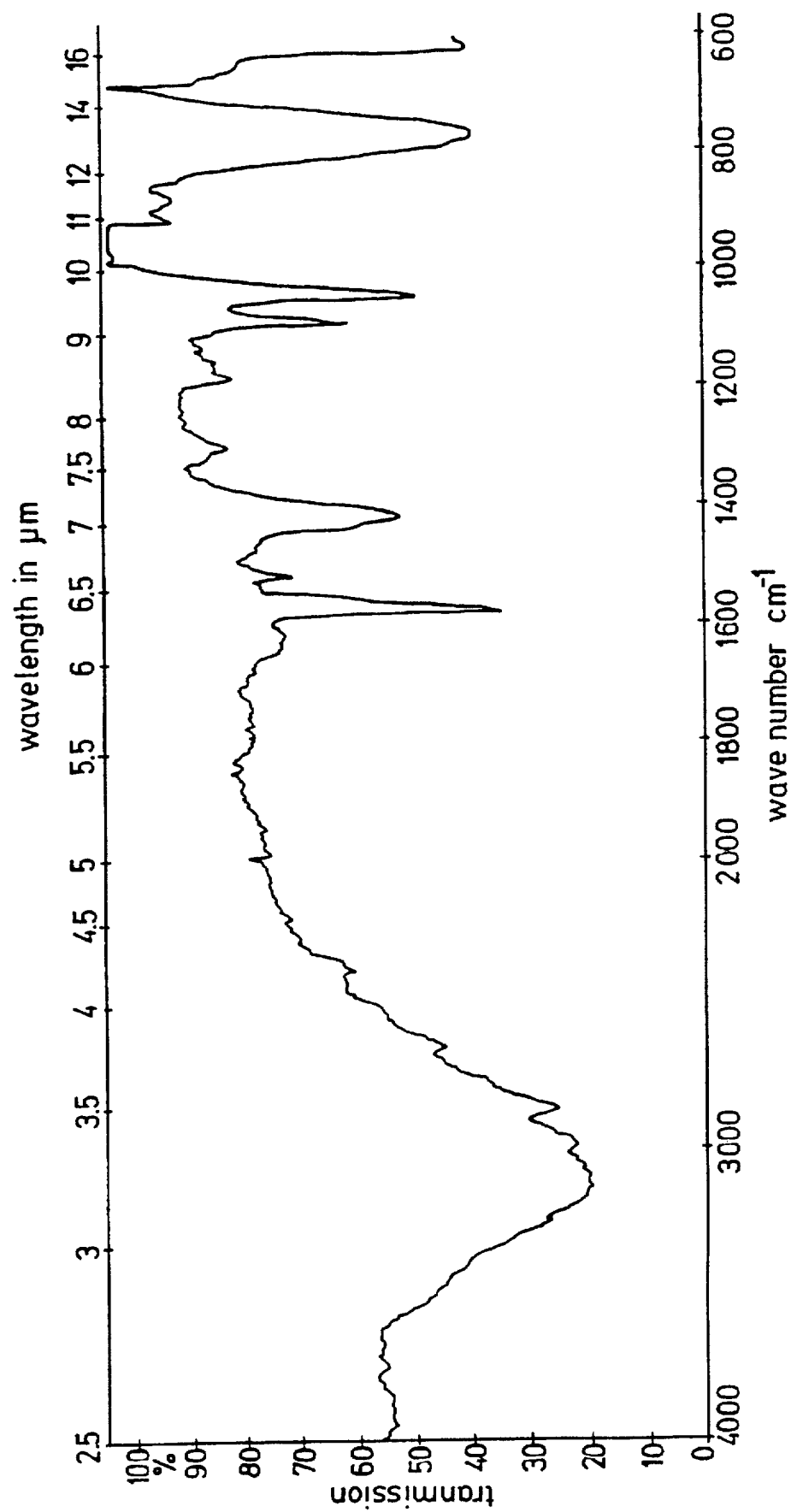

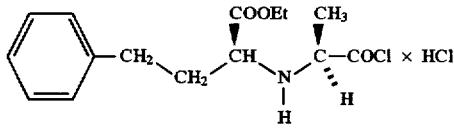

m.p. 119°–123° C., of the further reaction of the reagent (I) with N-[1-(S)-ethoxycarbonyl-3-phenylpropyl]-L-alanine and of the IR spectrum of imidazole hydrochloride (FIG. 2), the structure of the compound A may be inferred;

2) The novel compound A does not react with imidazole

The reactivity of N-[1-(S)-ethoxycarbonyl-3-phenylpropyl]-L-alanine acid chloride was tested and it was found that the reaction with imidazole was spontaneous and the imidazole hydrochloride was separated thereat. It is well-known from the literature that by such reactivity a further conversion to the corresponding aldehydes and ketones is made possible (*Liebigs Ann.* 655, 90, 1969; *Angew. Chem. Int. Ed.* 1, 351 1962; *Rec. Trav.* 84, 213, 1965).

3) The IR spectrum of the solid form of N-[1-(S)-ethoxycarbonyl-3-phenylpropyl]-L-alanine acid chloride (FIG. 5) shows oscillations at 1762 cm$^{-1}$ corresponding to the carbonyl group of the acid chloride, and oscillations at 1745 cm$^{-1}$ belonging to ester group.

4) The IR spectrum of the novel compound A (FIG. 3) does not show a signal at 1762 cm$^{-1}$ but only at 1745 cm$^{-1}$.

Figure 4:
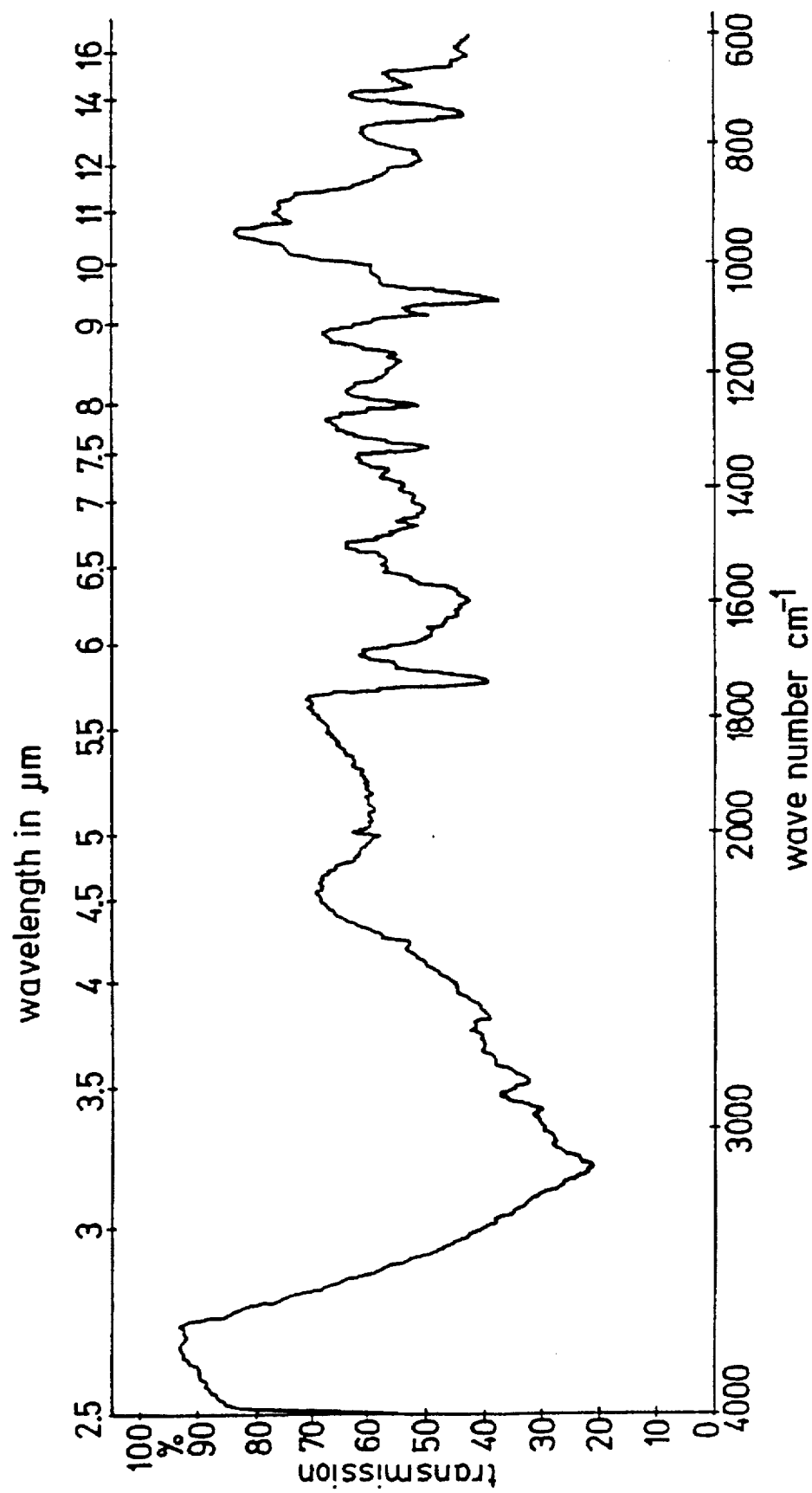

5) The IR spectrum of the novel compound A (FIG. 3) in the finger print area does not show that a mixture of N-[1-(S)-ethoxycarbonyl-3-phenylpropyl]-L-alanine acid chloride and imidazole could exist. The IR of the novel compound A (FIG. 3) has a very similar spectrum as the one of N-[1-(S)-ethoxycarbonyl-3-phenylpropyl]-L alanine imidazolide (B) (FIG. 4).

6) In the IR spectrum of the novel compound A (FIG. 3), an absorption band at 1625 cm$^{-1}$ can be noticed and in the spectrum of N-[1-(S)-ethoxycarbonyl-3-phenylpropyl]-L-alanine acid chloride, an oscillation at 1585 cm$^{-1}$ can be noticed (FIG. 5), which corresponds to >N$^+$H$_2$ and looks like an intramolecular hydrogen bond activated with the carbonyl group. The suggested structure blocks the amino group in N-[1-(S)-ethoxycarbonyl-3-phenylpropyl]-L-alanine acid chloride.

7) In the IR spectrum of imidazolide (FIG. 4), the absorption (conjugated —C=N— bond) at 1670 cm$^{-1}$ can be noticed; whereas in the IR spectrum of imidazole hydrochloride (FIG. 2) a vibration at 1580 cm$^{-1}$ can be noticed.

8) The reaction of N-[1-(S)-ethoxycarbonyl-3-phenylpropyl]-L-alanine acid chloride with disilylated L-proline takes place in the presence of triethylamine at 20°–25° C. in about 5 minutes to give enalapril maleate with a yield under 40%. The novel compound A (FIG. 3), however, reacts with disilylated L-proline under the same conditions essentially slower (more than 8 hours) with a yield over 80%. Also N-[1-(S)-ethoxycarbonyl-3-phenylpropyl]-L-alanine imidazolide (B) in the presence of imidazole hydrochloride and disilylated L-proline in 11 hours gives only the product with a 41% yield.

9) If to the novel compound A (IR spectrum in FIG. 3) dimethylacetamide sulfate (VI) was added, which sulfate blocks a secondary amino group, only 50% of enalapril maleate were isolated. The said reaction shows a special importance of the intramolecular hydrogen bond between the NH group and the carbonyl group.

10) In the presence of humidity or water, protic solvents or at elevated temperature, the compound A is converted to a novel compound C, which, however, reacts neiher with monosilylated and disilylated amino acids nor with salts of amino acids to the desired end products.

compound C: 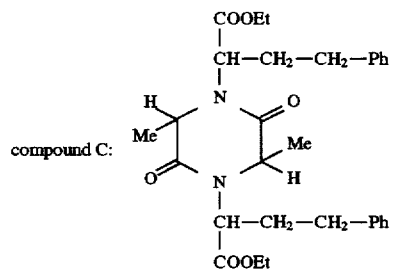

11) The compound C has a m.p. 109°–110° C. and is structurally a cyclic amide of the starting amino acid N-[1-(S)-ethoxycarbonyl-3-phenylpropyl]-L-alanine. It is formed quantitatively from intermediate A.

Figure 10:
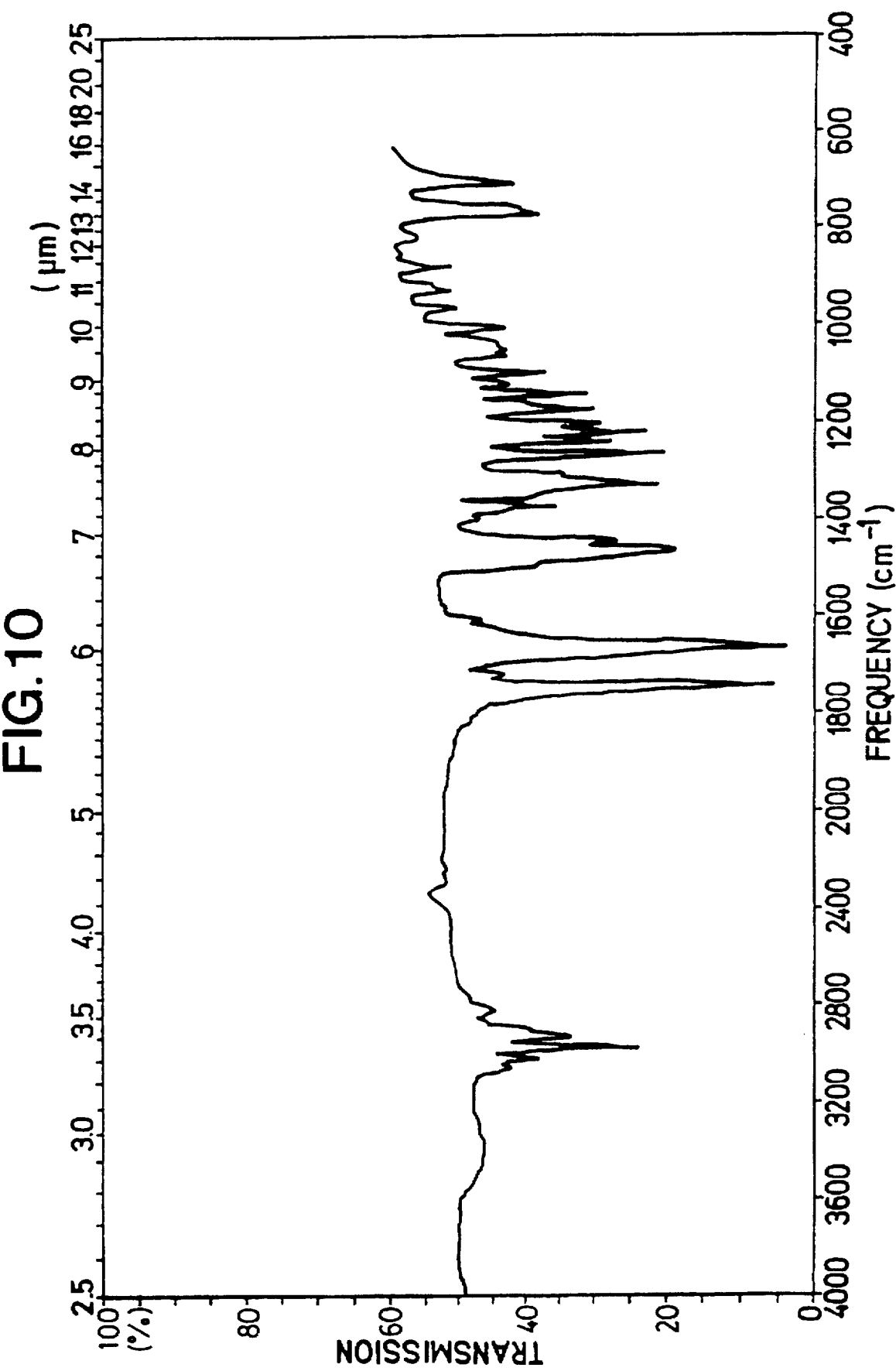
Figure 11:
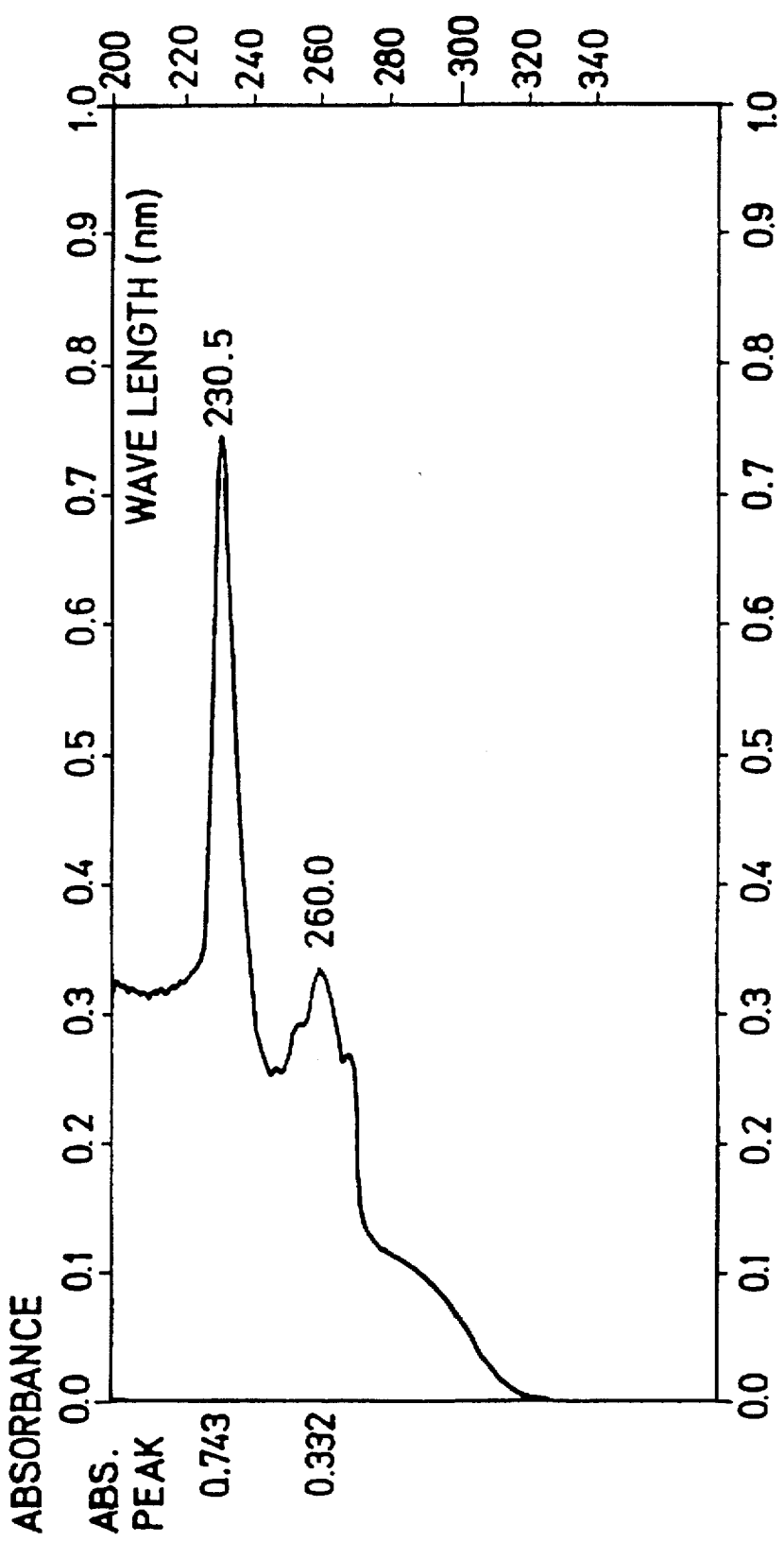

12) 1,4-di[(1-ethoxycarbonyl-3-phenyl)propyl-1]-3,6-dimethylpiperazine-2,5-dione (C) was characterized by NMR, IR (FIG. 10) and UV (FIG. 11) spectra, by elemental and mass analyses:

1. $^1$H—NMR (CDCl$_3$; TMS) 300 MHz: δ: 1.22 (t, 6H, —CH$_2$—CH$_3$), 1.55 (d, 6H, —CH—CH$_3$), 2.21–2.38 (m, 2H, Ph—CH$_2$—CH$_2$—CH), 2.42–2.58 (m, 2H, Ph—CH$_2$—CH$_2$—CH), 2.73 (m, 4H, Ph—CH$_2$—CH$_2$—CH), 3.76 (t, 1H, Ph—CH$_2$—CH$_2$—CH), 3.77 (t, 1H, Ph—CH$_2$—CH$_2$—CH), 3.86 (q, 2H, CH$_3$—CH), 4.12 (q, 2H, —CH$_2$—CH$_3$), 4.17 (q, 2H, —CH$_2$—CH$_3$), 7.10–7.25 (m, 10H, Ph).

2. $^{13}$C (CDCl$_3$, TMS) 300 MHz: δ: 14.24 (CH$_2$—CH$_3$), 19.59 (CH$_3$—CH), 30.81 (—CH$_2$—CH$_2$—Ph), 32.82

(—CH₂—CH₂—Ph), 58.93 (—CH—CH₃), 59.94 ( CH—CH₂), 61.73 (CH₂—CH₃), 126.57, 128.61, 128.68, 128.75, 128.89 (Ph), 167.26 (CO—N=), 169.96 ( COOEt).

Elemental analysis for $C_{30}H_{38}N_2O_6$:

| calc.: | 68.94% C | 7.33% H | 5.36% N |
|---|---|---|---|
| found: | 68.70% C | 7.18% H | 5.56% N |

Mass spectrum (T=150° C.) m/e: 522 (M⁺, 87%), 477 (M⁺—OEt, 17%), 449 (M⁺—COOEt, 8%), 418 (M⁺—Ph—CH₂—CH₂, 83%), 372 (M⁺—Ph—CH₂—CH₂—CH, 46%). m.p. 109°–110° C., M=522.12.

13) The reactions of forming activation reagents, activation of N-|1-(S)-ethoxycarbonyl-3-phenylpropyl|-L-alanine with activation reagents and reactions of disilylated amino acids with reagents A and B must be carried out in anhydrous aprotic solvents and at reduced temperature. Thus the formation of 1,4-di|(1-ethoxycarbonyl-3-phenyl)propyl-1|-3,6-dimethylpiperazine-2,5-dione (C) is avoided.

14) The reaction yield primarily depends upon the formation of the compound C. The formation of the compound C reduces the reaction yield.

Figure 12:
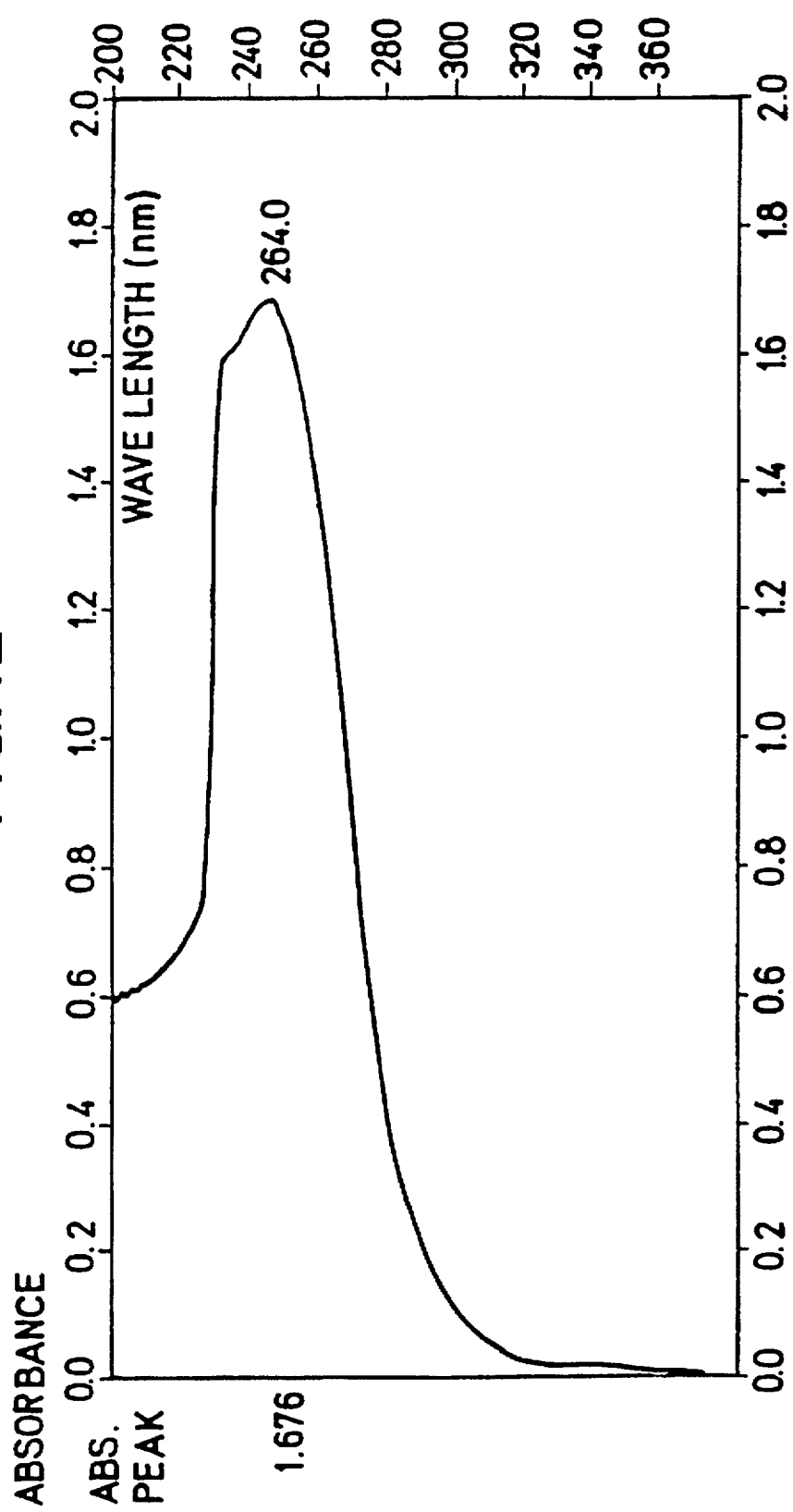

It follows from the above data that in the reaction between thionyl chloride and a) imidazole (from 1.1743 to 1.3486 g) via the formation of the reagent (I) and the subsequent reaction of the reagent (I) with N-|1-(S)-ethoxycarbonyl-3-phenylpropyl|-L-alanine a novel compound is isolated. On the basis of the experimental data and IR spectrum and on the basis of the comparison of the latter with the spectra of related compounds, there was suggested the structure A for the novel compound having the corresponding IR spectrum (FIG. 3), NMR spectrum and UV spectrum (FIG. 12)

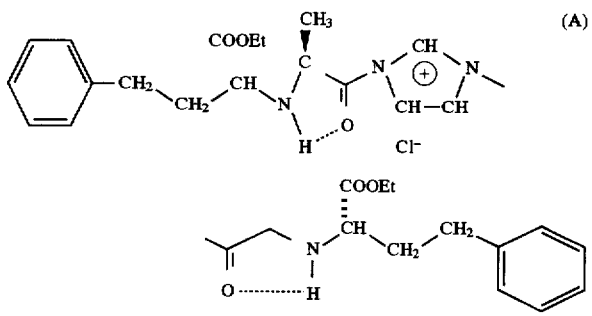

¹H—NMR (CH₂—CH₂, TMS) reaction mixture: δ: 1.15 (t, 6H, —CH₂—CH₃), 1.40 (d, 6H, —CH—CH₃), 1.80–2.10 (m, 2H, Ph—CH₂—CH₂—CH), 2.50–2.80 (m, 2H, Ph—CH₂—CH₂—CH), 3.22 (t, 2H, Ph—CH₂—CH₂—CH), 3.95 (q, 2H, —CH—CH₃), 4.12 (q, 4H, —CH₂—CH₃), 7.10–7.45 (m, 10H, Ph), 7.65 (d, 1H, H₄·), 7.70 (d, 1H, H₅·), 8.45 (m, 1H, H₂·). FAB⁺ (m/e): 591 (M⁺—HCl, 9%), 523 (10%), 234 (82%), 160 (15%), 150 (25%), 137 (42%), 117 (25%), 91 (57%), 69 (100%).

b) imidazole (2.4770 g) via reagent (II) and the subsequent reaction of the reagent with N-|1-(S)-ethoxycarbonyl-3-phenylpropyl|-L-alanine a novel compound having the structure B and IR spectrum (FIG. 4) is isolated.

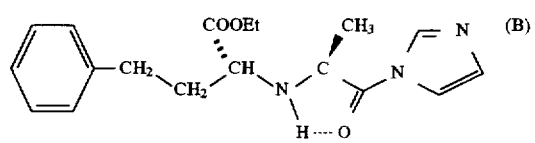

The structure of the novel intermediate compounds A or B and the system alone of running the reaction made possible the selectivity of the reaction, the absence of racemization and a high yield (at the compound A) of the reaction for preparing compounds having ACE inhibitory action according to the invention when compared to EP 0215335. The process alone is simple and industrially promising.

the invention is illustrated by the following Examples.

EXAMPLE 1

A) Process for the preparation of enalapril maleate
Preparation of reagent I

A solution (50 ml) of SOCl₂ (1 ml) in methylene chloride was prepared. The solution (22 ml) was portioned out and another 3 ml of dried methylene chloride (SOCl₂: 0.44 ml, 6.064 mmole) were added. The reaction mixture was cooled to −20° C. and to the reaction mixture a corresponding amount of imidazole (Table 3) was added. A slightly exothermic reaction was observed and the temperature rose to −15° C. The reaction was led according to Table 1. The solid precipitate was filtered off and washed with methylene chloride (5 ml). Imidazole hydrochloride was dried.

TABLE 1

| reaction time (min) | temperature (°C.) | remarks |
|---|---|---|
| 0 | −15 | white precipitate |
| 12 | −10 | white precipitate |
| 23 | −4 | white precipitate |
| 40 | +4 | white precipitate |
| 55 | +17 | white precipitate |
| 65 | +25 | white precipitate |

Activation of N-[1-(S)-ethoxycarbonyl-3-phenylpropyl]-L-alanine

N-|1-(S)-ethoxycarbonyl-3-phenylpropyl|-L-alanine (1.4 g) was added to the solution of reagent (I), stirred for 45 minutes at a temperature from −15° C. to 0° C. and then for 15 minutes at a temperature from 0° C. to +15° C. and finally for 5 minutes at a temperature from +15° C. to 20° C. (Table 2).

TABLE 2

| reaction time (min) | temperature (°C.) | remarks |
|---|---|---|
| 0 | −15 | suspension |
| 10 | −10 | |
| 25 | −5 | |
| 35 | −5 | |
| 45 | +1 | |
| 50 | +6 | |
| 60 | +12 | |
| 65 | +20 | |

After the completed reaction, the second filtration (amounts see Table 3) was carried out and the solids were washed with dry methylene chloride (5 ml).

Disilylation of L-proline

While preparing the intermediate A, a silylation of L-proline took place. A mixture of anhydrous methylene chloride (25 ml) and L-proline (0.69 g; not soluble in the solvent) and triethylamine (1.7 ml) was taken. Trimethylsilyl chloride (1.6 ml) was added to the reaction mixture. A slightly exothermic reaction was observed. Insoluble triethylammonium hydrochloride precipitated from the reaction mixture. The reaction mixture was stirred at room temperature for 150 minutes.

Acylation of N-|1-(S)-ethoxycarbonyl-3-phenylpropyl|-L-alanine

The reaction mixture of disilylated L-proline was added to the solution of the activated N-|1-(S)-ethoxycarbonyl-3-phenylpropyl|-L-alanine and the reaction mixture was stirred at room temperature (Table 3). The colour of the solution was from pale yellow to a darker colour.

Isolation

The solvent was evaporated on rotavapor. Water (10 ml) saturated with NaCl (3 g) was added. Ethyl acetate (5 ml) was added. The pH was adjusted from 6 to 4.2 with a 35% HCl solution. The yellowish organic phase was decanted and the aqueous phase was extracted with ethyl acetate (3×3 ml). The combined organic phases were dried over anhydrous sodium sulfate. If necessary, activated carbon was added to the solution. The solution was filtered off, washed with ethyl acetate (3×3 ml) and fresh solvent (4 ml) was added. Maleic acid (0.6 g) was added continuously. Enalapril maleate began to precipitate at once. The reaction mixture was stirred for 15 minutes at 25° C., cooled to −20° C. and stirred for another 20 minutes. The reaction mixture was left to warm to −15° C., filtered, washed with ethyl acetate (3 ml) and dried (Table 3).

TABLE 3

| imidazole (g) | imidazole hydrochloride (g) filtration | | L-proline (g) | time of acylation (h) | enalapril maleate | |
|---|---|---|---|---|---|---|
| | 1. | 2. | | | m (g) | yield (%) |
| a. 1 | 1.26 | — | 0.69 | 18 | 1.7 | 69.1 |
| b. 1 | 0.82 | 0.45 | 0.69 | 24 | 1.8 | 73.2 |
| c. 1.1743 | 1.26 | — | 0.69 | 18 | 1.77 | 72 |
| d. 1.1743 | 1.06 | 0.25 | 0.8 | 2 | 1.25 | 50.8 |
| e. 1.3486 | 1.18 | 0.03 | 0.69 | 2 | 1.67 | 67.8 |
| f. 1.3486 | 1.08 | 0.14 | 0.69 | 18 | 2 | 81.4 |
| g. 1.3486(1) | 1.08 | 0.14 | 0.69 | 18 | 1.27 | 51.6 |
| h. 1.1743 | 1.00 | 0.39 | 0.8 | 21 | 1.76 | 71.5 |
| i. 1.1743(2) | 1.06 | 1.02 | 0.8 | 18 | 1.23 | 50 |

Figure 7:
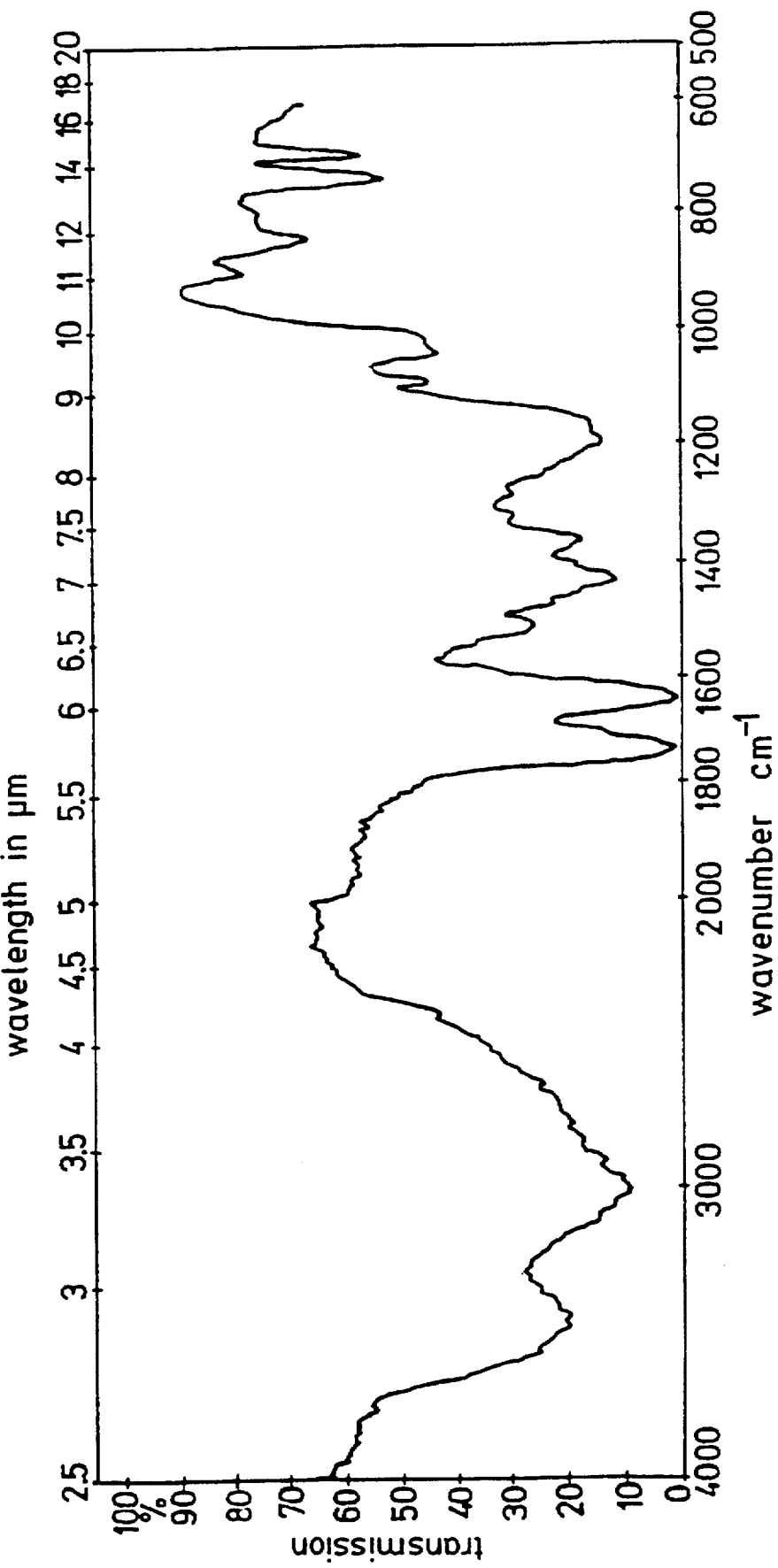

Remarks:
(1)acylation took place at 0–5° C.
(2)after activation, dimethylacetamide sulfate (VI) was added to the solution B) Process for the preparation of enalapril hydrochloride To a solution of enalapril in tertiary butyl methyl ether (prepared in the same way as in Example 1A before adding maleic acid, except for replacing ethyl acetate with tertiary butyl methyl ether as a solvent), gaseous HCl was added. Enalapril hydrochloride began to precipitate at once and was filtered off by suction. The salt was hygroscopic and had a m.p. 35° to 40° C. (IR FIG. 7).

C) Process for the preparation of enalapril sulfate

Figure 8:
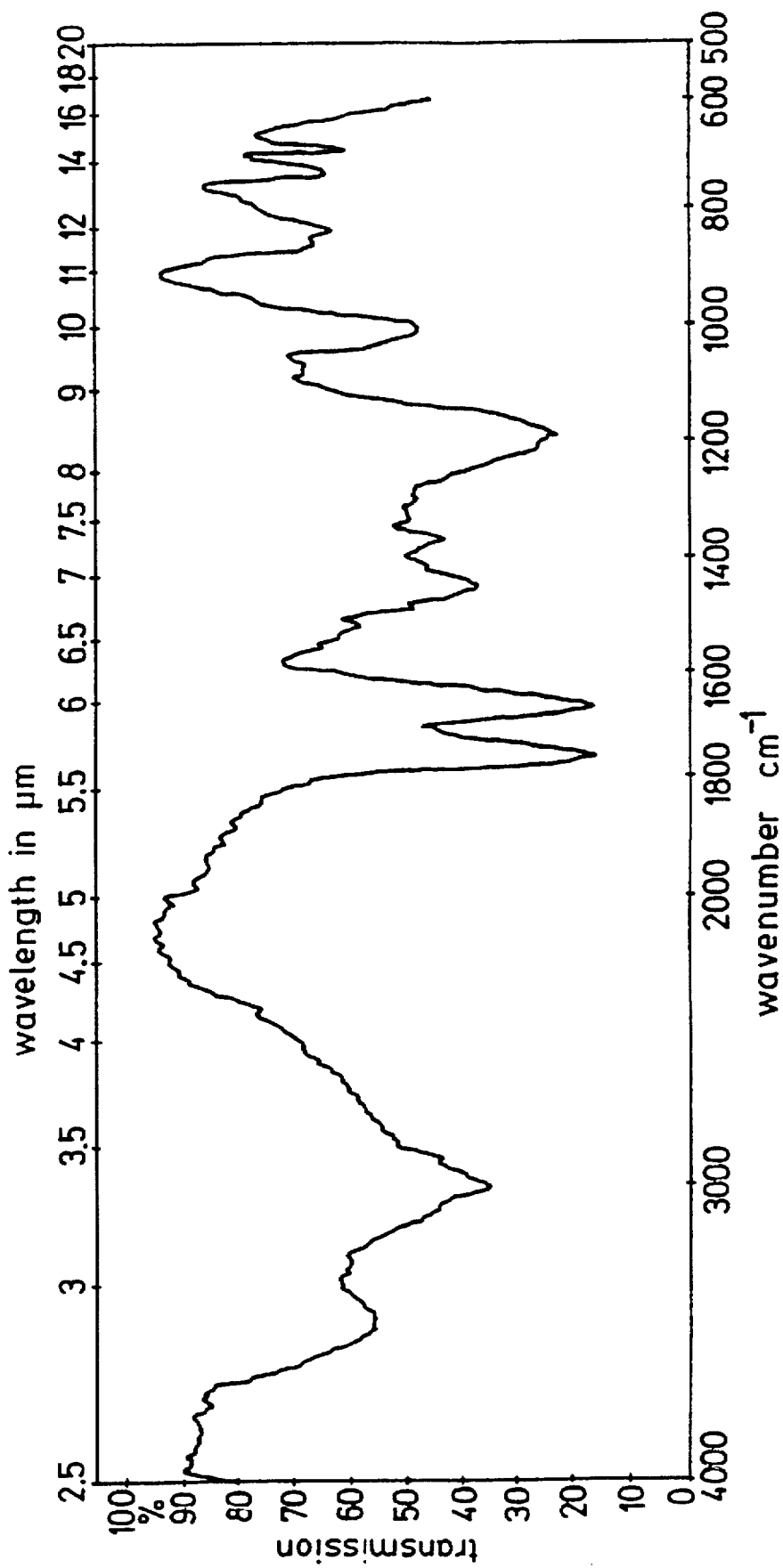

To a solution of 96% sulfuric (VI) acid (0.07 ml) in tertiary butyl methyl ether (2 ml), a solution of enalapril (1 g) in tertiary butyl methyl ether (10 ml) (prepared as in Example 1B) was added. The sulfate, which precipitated immediately, was filtered off (quantitatively), m.p. 70° to 88° C. (IR FIG. 8).

D) Process for the preparation of enalapril sodium salt

Figure 9:
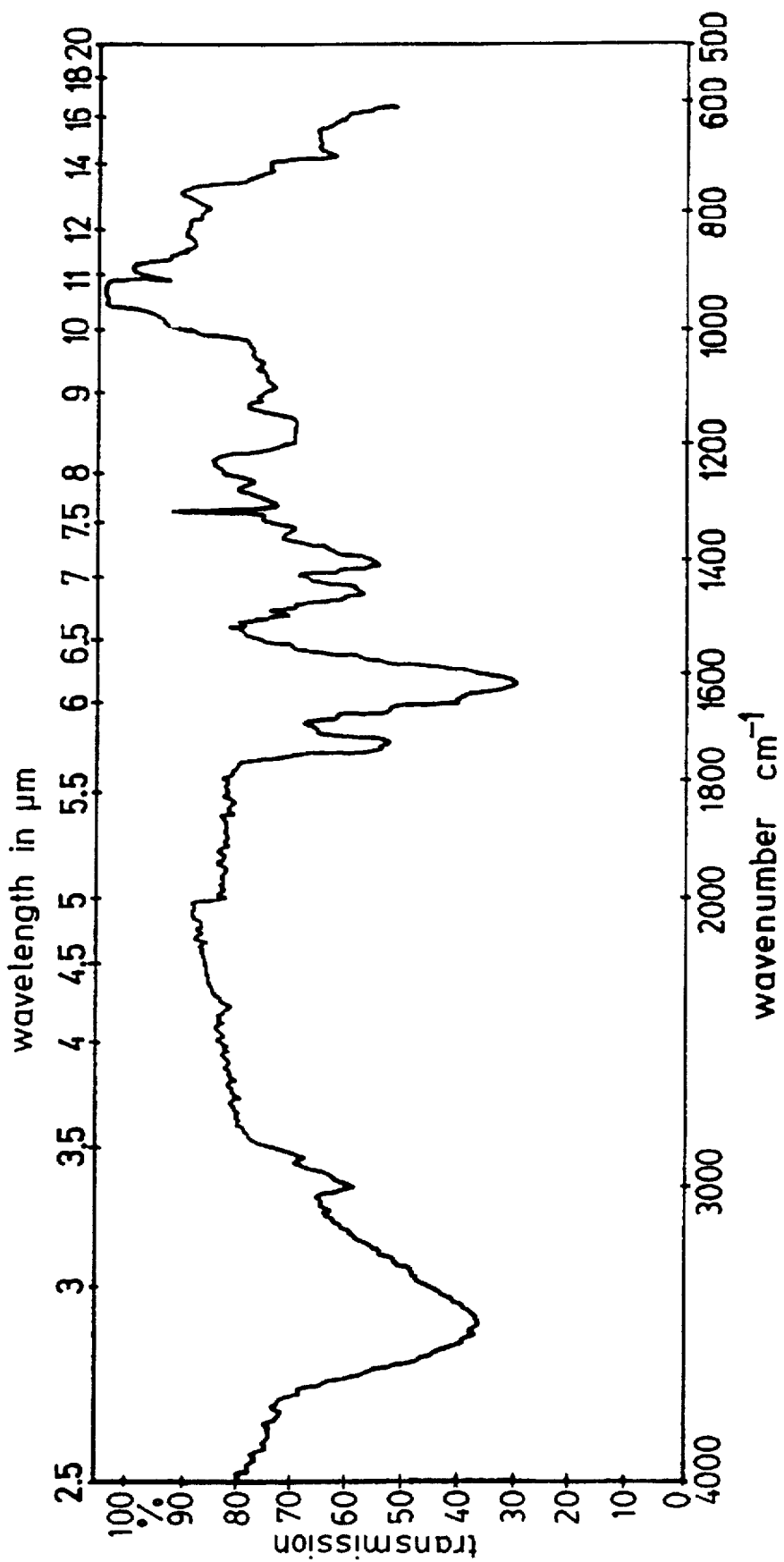

To methanol (5 ml) enalapril (0.35 g) and sodium methylate (0.05 g) were added. The reaction mixture was stirred for 10 minutes and then methanol was evaporated on rotavapor. A white precipitate (yield 100%) was isolated (IR FIG. 9).

EXAMPLE 2

It was proceeded in the same way as in the Example 1Af and after two filtrations of imidazole hydrochloride, additional imidazole (0.693 g) was added to the system. No precipitation of imidazole hydrochloride was observed. After 20 hours of the reaction, enalapril maleate (1.24 g; 50%) was isolated. Thus the increased concentration of imidazole reduced the final yield.

EXAMPLE 3

It was proceeded in the same way as in Example 1Af except that only one filtration of imidazole hydrochloride was made. The reaction time was 20 hours at room temperature. The reaction mixture became dark red. The reaction yield was 57.3% or 1.41 g.

EXAMPLE 4

Process for the preparation of enalapril maleate (using reagent (II))

Methylene chloride (22 ml) containing thionyl chloride (0.44 ml) was diluted to 25 ml. Imidazole (2.4769 g) was added. The reaction time and the reaction conditions were the same as in Example 1. Imidazole hydrochloride (0.41 g) was filtered off. N-[1-(S)-ethoxycarbonyl-3-phenylpropyl]-L-alanine (1.4 g) was activated with reagent (II) to intermediate B and the reaction with disilylated L-proline was carried out as in Example 1. After the completed reaction, enalapril maleate (1.72 g or 41.4%) was isolated. The melting point of enalapril maleate as measured was 144°–148° C. The melting point mentioned in the literature is 143°–144.5° C.

EXAMPLE 5

Process for the preparation of diquinalapril sulfate

Preparation of reagent (I)

A solution (50 ml) of $SOCl_2$ (1 ml) in methylene chloride was prepared. The solution (22 ml) was portioned out and there were added another 3 ml of dried methylene chloride ($SOCl_2$: 0.44 ml, 6.064 mmole). The reaction mixture was cooled to −15° C. and to the reaction mixture imidazole (1.348 g, 19.81 mmole) was added. The reaction was led according to Table 4. The solid precipitate was filtered off and washed with cooled methylene chloride (5 ml). Imidazole hydrochloride (1.14 g) was dried.

TABLE 4

| reaction time (min) | temperature (°C.) | remarks |
|---|---|---|
| 0 | −15 | white precipitate |
| 12 | −10 | white precipitate |
| 23 | −4 | white precipitate |
| 40 | +4 | white precipitate |
| 55 | +17 | white precipitate |
| 65 | +25 | white precipitate |

Activation of N-|1-(S)-ethoxycarbonyl-3-phenylpropyl|-L-alanine

N-[1-(S)-ethoxycarbonyl-3-phenylpropyl]-L-alanine (1.4 g) was added to the slightly coloured solution of reagent (I), stirred for 45 minutes at a temperature from −15° C. to 0° C. and then for 15 minutes at a temperature from 0° C. to +15°

C. and finally for 5 minutes at a temperature from +20° C. to 25° C. After the completed reaction, insoluble particles were filtered off and washed with cooled dry methylene chloride (5 ml). The precipitate (0.14 g) was isolated.

Disilylation of 1,2,3,4-tetrahydro-3-isoquinolinecarboxylic acid

A mixture of anhydrous methylene chloride (25 ml), 1,2,3,4-tetrahydro-3-iso-quinolinecarboxylic acid hydrochloride (1,2,3,4-tetrahydro-3-isoquinolinecarboxylic acid hydrochloride, not soluble in the solvent) (1.7 g) and triethylamine (2.1 ml) was taken. Trimethylsilyl chloride (1.6 ml) was added to the reaction mixture. A slightly exothermic reaction was observed., Insoluble triethylammonium hydrochloride precipitated from the reaction mixture. The reaction mixture was stirred at room temperature for 2 hours.

Acylation

A suspension of disilylated 1,2,3,4-tetrahydro-3-isoquinolinecarboxylic acid was added to the reaction mixture and the obtained yellowish reaction mixture was stirred for 18 hours at room temperature.

Isolation

Figure 6:
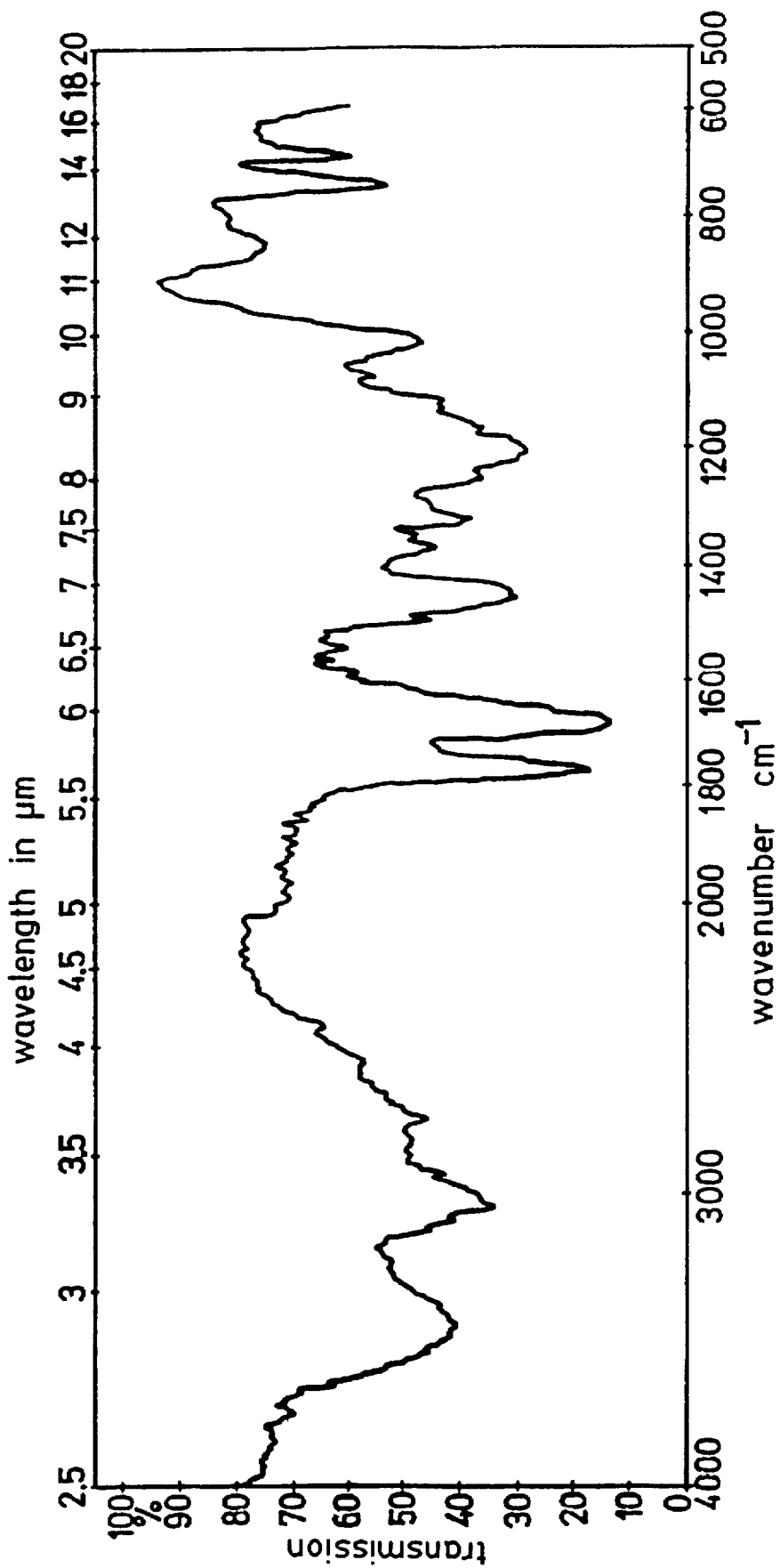

The solvent was evaporated to dryness on rotavapor after 18 hours of stirring and water (10 ml) saturated with sodium chloride was added. Methylene chloride (10 ml) was added to the mixture. The pH of the solution was adjusted from 6 to 4.2 with concentrated hydrochloric acid. The aqueous phase was washed with methylene chloride (2×5 ml). The organic phases were combined, dried with anhydrous sodium sulfate and filtered. A solution of tertiary butyl methyl ether (3 ml) and 96% sulfuric (VI) acid (0.1 ml) was added to the methylene chloride solution. The solvents were evaporated on rotavapor and diquinalapril sulfate (2.56 g) was isolated with a 92% yield and m.p. 90° C. (IR FIG. 6).

EXAMPLE 6

A solution of $SOCl_2$ (2.2 ml) in anhydrous methylene chloride (125 ml) (treatment with 96% $H_2SO_4$ and distillation) was prepared. The reaction mixture was cooled to −15° C., imidazole (6.7430 g) was added and the reaction was led according to the following Table 5.

TABLE 5

| reaction time (min) | temperature (°C.) | remarks |
| --- | --- | --- |
| 0 | −15 | white precipitate |
| 12 | −10 | white precipitate |
| 23 | −4 | white precipitate |
| 40 | +4 | white precipitate |
| 55 | +17 | white precipitate |
| 65 | +20 to +25 | white precipitate |

The precipitate was filtered off and washed with anhydrous methylene chloride (10 ml). The solution was cooled to −15° C. and N-[1-(S)-ethoxycarbonyl-3-phenyl-propyl]-L-alanine (7 g) was added. The reaction was led according to Table 6.

TABLE 6

| reaction time (min) | temperature (°C.) | remarks |
| --- | --- | --- |
| 0 | −15 | opalescent solution |
| 15 | −10 | opalescent solution |
| 30 | −5 | opalescent solution |
| 45 | 0 | opalescent solution |

TABLE 6-continued

| reaction time (min) | temperature (°C.) | remarks |
| --- | --- | --- |
| 50 | +5 | opalescent solution |
| 55 | +10 | opalescent solution |
| 60 | +15 | opalescent solution |
| 65 | +20 to +25 | opalescent solution |

The insoluble particles were filtered off and washed with anhydrous methylene chloride (10 ml). The prepared solution of silylated L-proline was added to the solution. The light yellow solution was stirred at room temperature (21° C.) for 22 hours. The solvent was evaporated to dryness at a temperature of 30°–35° C. and saturated aqueous sodium chloride solution (50 ml $H_2O$ and 17 g NaCl) and ethyl acetate (25 ml) (pH 5.08) were added to the residue. It was acidified to pH 4.22 with concentrated hydrochloric acid. The aqueous phase and ester phase were separated and the aqueous phase was washed with ethylacetate (2×15 ml), the organic phases were combined and dried with anhydrous sodium sulfate. It was filtered and washed with ethyl acetate (2×15 ml). Maleic acid (3 g) was added to the solution and enalapril maleate precipitated. The reaction mixture was stirred for another 15 minutes at room temperature, then it was cooled to −25° C. and after 15 minutes at this temperature the precipitate was filtered and washed with ethyl acetate (10 ml). Enalapril maleate (11.2 g; 90.73%) was obtained.

Silylation of L-proline

L-proline (3.45 g) was dissolved in anhydrous methylene chloride (125 ml), trimethylamine (3.5 ml) and trimethylchlorosilane (8 ml) were added. The reaction mixture was stirred at room temperature for 90 minutes.

EXAMPLE 7

It was proceeded in the same way as in Example 6 except that silylated L-proline was prepared in a different manner.

Silylation of L-proline

L-proline (0.69 g), triethylamine (0.9 ml) and trimethylsilylchloride (1.6 ml) were added to methylene chloride (25 ml). The reaction mixture was stirred at room temperature for 2 hours.

Enalapril maleate (1.96 g or 79.39%) was isolated.

EXAMPLE 8

It was proceeded in the same way as in Example 6 except that silylated L-proline was prepared in a different manner.

Silylation of L-proline

L-proline (0.69 g) and trimethylsilylchloride (1.6 ml) were added to methylene chloride (25 ml). The reaction mixture was stirred at room temperature for 2 hours.

Enalapril maleate (1.32 g or 53.47%) was isolated.

EXAMPLE 9

It was proceeded in the same way as in Example 6 except that silylated L-proline was prepared in a different manner.

Silylation of L-proline

L-proline (0.69 g), triethylamine (0.5 ml) and trimethylsilylchloride (1.6 ml) were added to methylene chloride (25 ml). The reaction mixture was stirred at room temperature for 2 hours.

Enalapril maleate (1.81 g or 73.31%) was isolated.

The results of Examples 6 to 9 show that the best reaction yield was achieved when such a solution of silylated L-proline entered the reaction mixture wherein disilyllated L-proline i.e. L-proline-N-trimethylsilyl-O-trimethylsilyl ester, and monosilylated L-proline i.e. L-proline-O-trimethylsilylester hydrochloride were in a 1:1 ratio.

The following Examples 10 and 11 illustrate the process wherein imidazole was replaced by benzimidazole and 2-methylimidazole in the preparation of the reagent for activating N-|1-(S)-ethoxycarbonyl-3-phenylpropyl|-L-alanine.

EXAMPLE 10

Preparation of activating reagent on the basis of benzimidazole

A solution (50 ml) of $SOCl_2$ (1 ml) in methylene chloride was prepared. The solution (22 ml) was portioned out and there were added another 3 ml of dried methylene chloride ($SOCl_2$: 0.44 ml, 6.064 mmole). The reaction mixture was cooled to −15° C. and to the reaction mixture benzimidazole (2.340 g, 19.81 mmole). was added. The reaction was led according to Table 7.

TABLE 7

| reaction time (min) | temperature (°C.) | remarks |
| --- | --- | --- |
| 0 | −15 | white precipitate |
| 12 | −10 | white precipitate |
| 23 | −4 | white precipitate |
| 40 | +4 | white precipitate |
| 55 | +17 | white precipitate |
| 65 | +25 | white precipitate |

The solid precipitate was filtered and washed with cooled methylene chloride (5 ml). N-[1-(S)-ethoxycarbonyl-3-phenylpropyl]-L-alanine (1.4 g) was added to the solution cooled to −15° C. and it was stirred for 45 minutes at a temperature from −15° C. to 0° C., then for 15 minutes at a temperature from 0° C. to +15° C. and further for 5 minutes at a temperature from +20° C. to +25° C. After the completed reaction insoluble particles were filtered off and washed with cooled dry methylene chloride (5 ml). A suspension of disilylated L-proline was added to the reaction mixture and it was stirred at room temperature for 18 hours.

After 18 hours of stirring, the solvent was evaporated to dryness on rotavapor and a saturated sodium chloride solution (10 ml) was added. Ethyl acetate (10 ml) was added to the mixture and the pH of the solution was adjusted from 6 to 4.2 with concentrated hydrochlorid acid. The aqueous phase was washed with ethyl acetate (2×3 ml). The organic phases were combined, dried with anhydrous sodium sulfate and filtered. Maleic acid (0.6 g) in ethyl acetate (4 ml) was added to the ethyl acetate solution. The solution was stirred at room temperature for 20 minutes and then cooled to −20° C. for another 20 minutes. The obtained precipitate was filtered, washed with ethyl acetate and dried. Enalapril maleate was isolated with a good yield and a purity of >99%.

Preparation of disilylated L-proline

L-proline (0.69 g), methylene chloride (25 ml), triethylamine (0.7 ml) and trimethylsilylchloride (1.6 ml) were blended. The reaction mixture was stirred at room temperature for 2 hours.

EXAMPLE 11

Preparation of activating agent on the basis of 2-methylimidazole

A solution (50 ml) of $SOCl_2$ (1 ml) in methylene chloride was prepared. The solution (22 ml) was portioned out and another 3 ml of dried methylene chloride ($SOCl_2$: 0.44 ml, 6.064 mmole) were added. The reaction mixture was cooled to −15° C. and to the reaction mixture 2-methylimidazole (1.623 g, 19.81 mmole) was added. The reaction was led according to Table 8.

TABLE 8

| reaction time (min) | temperature (°C.) | remarks |
| --- | --- | --- |
| 0 | −15 | white precipitate |
| 12 | −10 | white precipitate |
| 23 | −4 | white precipitate |
| 40 | +4 | white precipitate |
| 55 | +17 | white precipitate |
| 65 | +25 | white precipitate |

The solid precipitate was filtered and washed with cooled methylene chloride (5 ml). N-[1-(S)-ethoxycarbonyl-3-phenylpropyl]-L-alanine (1.4 g) was added to the solution cooled to −15° C. and it was stirred for 45 minutes at a temperature from −15° C. to 0° C., then for 15 minutes at a temperature from 0° C. to +15° C. and further for 5 minutes at a temperature from +20° C. to +25° C. After the completed reaction, insoluble particles were filtered off and the solid filtrate was washed with cooled dry methylene chloride (5 ml). A suspension of disilylated L-proline was added to the reaction mixture and it was stirred at room temperature for 18 hours.

After 18 hours of stirring, the solvent was evaporated to dryness on rotavapor and a saturated sodium chloride solution (10 ml) was added. Ethyl acetate (10 ml) was added to the mixture and the pH of the solution was adjusted from 6 to 4.2 with concentrated hydrochlorid acid. The aqueous phase was washed with ethyl acetate (2×3 ml). The organic phases were combined, dried with anhydrous sodium sulfate and filtered. Maleic acid (0.6 g) in ethyl acetate (4 ml) was added to the ethyl acetate solution. The solution was stirred at room temperature for 20 minutes and then cooled to −20° C. for another 20 minutes. The obtained precipitate was filtered, washed with ethyl acetate and dried. Enalapril maleate was isolated with a good yield and a purity of >99%.

We claim:

1. Process for the preparation of compounds having ACE inhibitory action of the formula

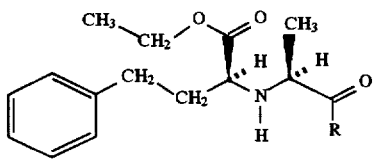

and pharmaceutically acceptable salts thereof, wherein R has the following meanings

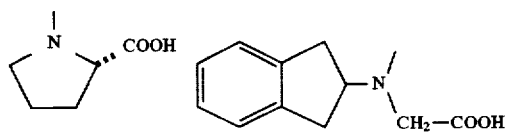

17

-continued

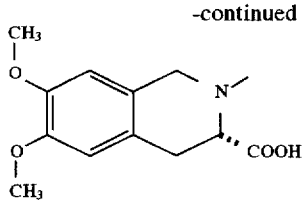

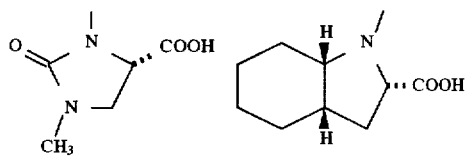

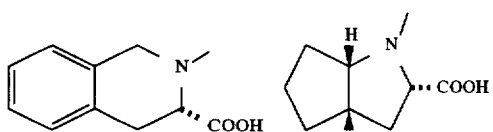

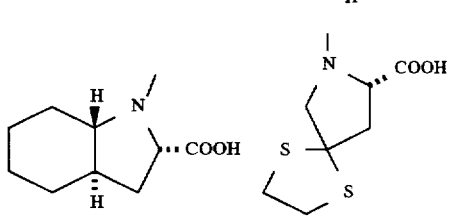

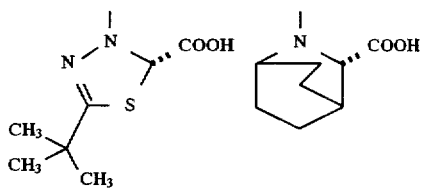

characterized in that the carboxy group of the stereospecific amino acid N-[1-(S)-ethoxycarbonyl-3-phenylpropyl]-L-alanine of the formula

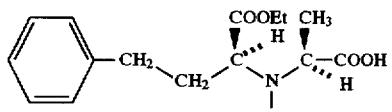

is activated with thionyl chloride derivative of the formula I'

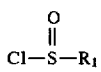 (I')

or with thionyl chloride derivative of the formula II'

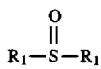 (II')

wherein $R_1$ is the residue of a heterocyclic ambident compound, in the presence of an aprotic organic solvent under elimination of the precipitated hydrochloride of the above mentioned heterocyclic ambident compound, to the intermediate novel compound A

18

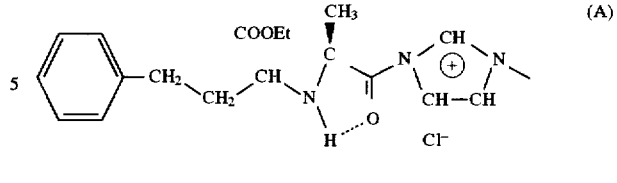 (A)

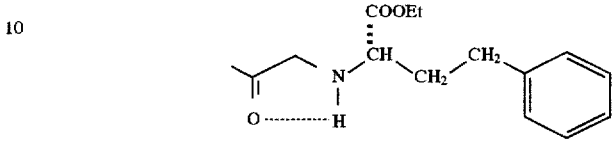

or to the intermediate novel compound B

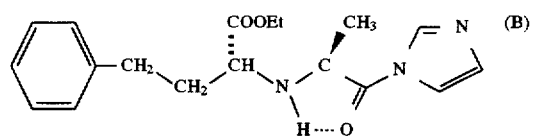 (B)

and the obtained A or B intermediate compound is reacted with an amino acid, selected from the group which consists of

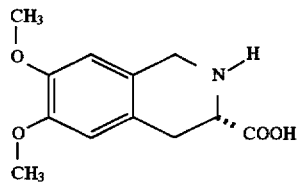

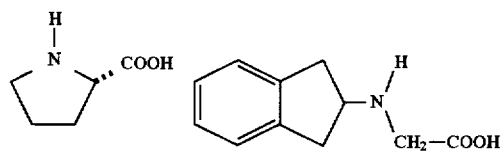

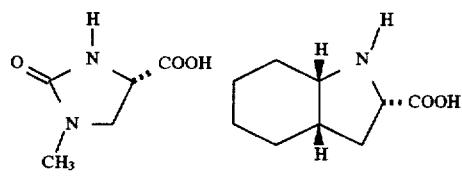

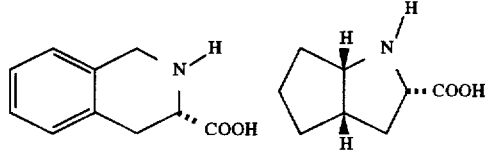

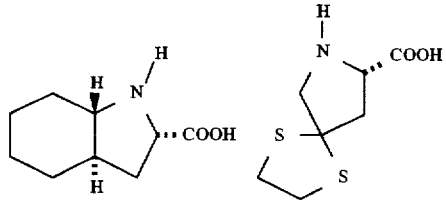

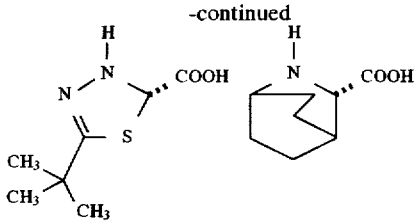

whereat the reaction medium must be anhydrous in all steps, and then the obtained compounds are converted to pharmaceutically acceptable salts thereof in a conventional manner.

2. Process according to claim 1, characterized in that the compound of formula I' is a chlorothionylimidazole of the formula (I)

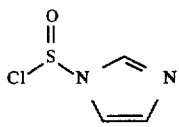

is used.

3. Process according to claim 1, characterized in that as the compound of the formula II' thionyldiimidazole of the formula (II)

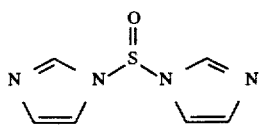

is used.

4. Process according to claim 1, characterized in that for the reaction with amino acid a mixture of monosilylated amino acid and disilylated amino acid is used, preferably in a 1:1 ratio.

5. Process according to claim 1, characterized in that as amino acid L-proline in the form of a mixture of disilylated and monosilylated L-proline is used.

6. Process according to claim 1, characterized in that disilylated L-proline, and monosilylated L-proline are in a 1:1 ratio.

7. Compound of the formula A

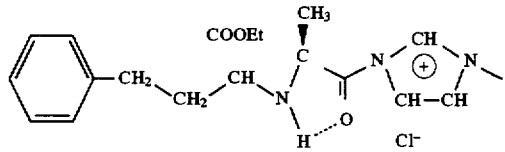

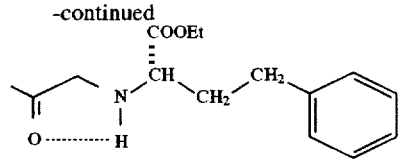

8. Compound of the formula B

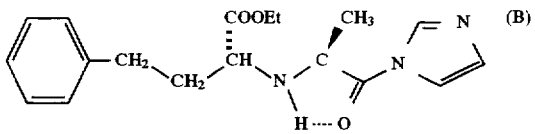

9. Process according to claim 1, characterized in that for the reaction with amino acid a mixture of monosilylated amino acid and disilylated amino acid is used in a 1:1 ratio.

10. Process according to claim 6, characterized in that said disilylated L-proline is L-proline-N-trimethylsilyl-O-trimethylsilyl ester, and said monosilylated L-proline is L-proline-O-trimethylsilylester hydrochloride.

11. Process according to claim 2, characterized in that for the reaction with amino acid a mixture of monosilylated amino acid and disilylated amino acid is used.

12. Process according to claim 2, characterized in that as amino acid L-proline in the form of a mixture of disilylated and monosilylated L-proline is used.

13. Process according to claim 3, characterized in that as amino acid L-proline in the form of a mixture of disilylated and monosilylated L-proline is used.

14. Process according to claim 4, characterized in that as amino acid L-proline in the form of a mixture of disilylated and monosilylated L-proline is used.

15. Process according to claim 14, characterized in that said mixture is in a 1:1 ratio.

16. Process according to claim 11, characterized in that said mixture is in a 1:1 ratio.

17. The process of claim 1 wherein said heterocyclic ambident compound is selected from the group consisting of imidazole, benzimidazole, 2-methylimidazole and triazole.

18. The process of claim 17 wherein said amino acid is in a monosilylated form.

19. The process of claim 17 wherein said amino acid is in a disilylated form.

20. The process of claim 1 wherein said amino acid is in a monosilylated form.

21. The process of claim 1 wherein said amino acid is in a disilylated form.

* * * * *